United States Patent
Walker et al.

(10) Patent No.: US 6,652,491 B1
(45) Date of Patent: Nov. 25, 2003

(54) STEERABLE STYLET

(75) Inventors: Gregory L. Walker, Whitestown, IN (US); John A. Steen, Zionsville, IN (US)

(73) Assignee: Catheter Research, Inc., Indianapolis, IN (US)

( * ) Notice: Subject to any disclaimer, the term of this patent is extended or adjusted under 35 U.S.C. 154(b) by 0 days.

(21) Appl. No.: 09/848,745

(22) Filed: May 3, 2001

(51) Int. Cl.[7] ............................................. A61M 5/178
(52) U.S. Cl. ........................ 604/164.01; 604/164.13; 604/170.02; 604/530
(58) Field of Search ......................... 604/19–21, 27, 604/36, 48, 506–510, 93.01, 164.01–164.13, 170.01, 170.02, 264, 523–528, 530–536

(56) References Cited

U.S. PATENT DOCUMENTS

| | | | |
|---|---|---|---|
| 3,890,977 A | * | 6/1975 | Wilson .................. 604/21 |
| 4,543,090 A | | 9/1985 | McCoy |
| 4,601,705 A | | 7/1986 | McCoy |
| 4,758,222 A | | 7/1988 | McCoy |
| 4,777,799 A | | 10/1988 | McCoy et al. |
| 4,918,919 A | | 4/1990 | McCoy et al. |
| 4,944,727 A | | 7/1990 | McCoy |
| 5,055,101 A | | 10/1991 | McCoy |
| 5,090,956 A | | 2/1992 | McCoy |
| 5,114,402 A | | 5/1992 | McCoy |
| 5,135,517 A | | 8/1992 | McCoy |
| 5,188,111 A | | 2/1993 | Yates et al. |
| 5,242,394 A | | 9/1993 | Tremulis |
| 5,334,168 A | | 8/1994 | Hemmer |
| 5,529,067 A | * | 6/1996 | Larsen et al. ............ 600/374 |
| 5,531,685 A | | 7/1996 | Hemmer et al. |
| 5,722,425 A | | 3/1998 | Boström |
| 5,755,663 A | * | 5/1998 | Larsen et al. ............ 600/374 |
| 5,885,258 A | * | 3/1999 | Sachdeva et al. ........ 600/141 |
| 5,885,278 A | | 3/1999 | Fleischman |
| 5,899,932 A | * | 5/1999 | Dann et al. .............. 606/28 |
| 5,904,657 A | | 5/1999 | Unsworth et al. |
| 5,931,819 A | | 8/1999 | Fariabi |
| 5,957,966 A | | 9/1999 | Schroeppel et al. |
| 5,967,976 A | * | 10/1999 | Larsen et al. ............ 600/374 |
| 5,987,360 A | * | 11/1999 | McGrath et al. .......... 606/28 |
| 6,023,638 A | * | 2/2000 | Swanson ................. 600/510 |
| 6,036,631 A | * | 3/2000 | McGrath et al. .......... 600/3 |
| 6,072,154 A | | 6/2000 | Maynard |
| 6,096,036 A | * | 8/2000 | Bowe et al. ............. 600/372 |
| 6,123,083 A | * | 9/2000 | McGrath et al. .......... 128/898 |
| 6,146,381 A | * | 11/2000 | Bowe et al. ............. 600/374 |
| 6,223,085 B1 | * | 4/2001 | Dann et al. .............. 606/29 |
| 6,270,496 B1 | * | 8/2001 | Bowe et al. ............. 128/898 |

* cited by examiner

Primary Examiner—Ira S. Lazarus
Assistant Examiner—Andrea M. Ragonese
(74) Attorney, Agent, or Firm—Bose McKinney & Evans LLP

(57) ABSTRACT

A medical device is provided that includes a catheter and a stylet positioned in the catheter. The stylet is configured to guide the catheter through a passage of a patient. The stylet is preferable tubular and made of a shape-memory material that changes shape when heated to bend or turn the catheter.

57 Claims, 5 Drawing Sheets

STEERABLE STYLET

BACKGROUND AND SUMMARY OF THE INVENTION

The present invention relates to medical devices. More specifically the present invention relates to catheters and stylets used to steer the distal tips of catheters.

During some medical procedures, it is necessary for a surgeon to insert a device into a patient through a passage within the patient. Because the passages often bend and turn as they extend through the patient, it is often necessary to guide or otherwise steer the device through the passage to avoid damaging the passages or to position the device in a desired location in the passage.

The implantation of a pacemaker is one example of such a medical procedure. For example, during the implantation of a pacemaker, a cardiologist guides a pacemaker lead through veins into a patient's heart. Once the pacemaker lead is guided into the patient's heart, the cardiologist guides the pacemaker lead within the chambers of the heart to a specific location where the pacemaker lead is attached to one of the muscular walls of the heart.

According to the present invention, a medical device is provided that is configured to be inserted into a passage of a patient. The medical device includes a catheter formed to include a lumen therein and a stylet. The stylet includes a tubular member made of a shape-memory material configured to alter a physical characteristic of the catheter in response to activation of the shape-memory material.

According to another embodiment of the present invention, a device is provided that includes a flexible, elongated tubular member having a central axis extending therethrough and a stylet. The stylet includes a shape-memory tube made of shape-memory material and formed to include a lumen extending therethrough. The shape-memory tube is positioned in the tubular member to permit movement of the shape-memory tube relative to the tubular member along the central axis.

According to another embodiment of the present invention, a device is provided that includes a tubular member having a lumen formed therein and a shape-memory member having a lumen formed therein. The shape-memory member is removably received in the lumen of the tubular member. The shape-memory member is movable in response to a change in temperature of the shape-memory member. The shape of the tubular member changes upon movement between the first and second positions.

According to another embodiment of the present invention, a device is provided that is configured to be inserted into a passage of a patient. The apparatus includes a flexible, elongated member having a distal end configured to be inserted into a passage of a patient. The flexible, elongated member includes a primary member, a secondary member, and means for coupling the primary member to the secondary member. The primary member includes a lumen formed therein and is made of a shape-memory material.

According to the present invention, a method for steering a catheter is provided. The method includes the steps of inserting a temperature activated shape-memory tube into a lumen of a catheter; activating the shape-memory tube by changing the temperature of the shape-memory tube from a first temperature to a second temperature different than the first temperature; and removing the shape-memory tube from the catheter.

Additional features of the disclosure will become apparent to those skilled in the art upon consideration of the following detailed description when taken in conjunction with the accompanying drawings.

BRIEF DESCRIPTION OF THE DRAWINGS

FIG. 4 is cross-sectional view of a portion of a first embodiment stylet showing the stylet including a distal primary member made of nitinol tube, a proximal secondary member made of stainless steel tube, and a copper wire positioned in the nitinol and stainless steel tubes and the nitinol and stainless steel tubes forming a butt joint therebetween;

FIG. 5 is cross-sectional view of a portion of a second embodiment stylet showing the stylet including a distal primary member made of nitinol tube and a proximal secondary member made of stainless steel tube and the nitinol and stainless steel tubes forming a lap joint therebetween;

FIG. 6 is cross-sectional view of a portion of a third embodiment stylet showing the stylet including a distal primary member made of nitinol tube, a proximal secondary member made of stainless steel tube, and a copper wire positioned in the nitinol and stainless steel tubes and the nitinol and stainless steel tubes forming a lap joint therebetween;

FIG. 7 is cross-sectional view of a portion of a fourth embodiment stylet showing the stylet including a distal primary member made of nitinol tube, a proximal secondary member made of stainless steel tube, a first copper wire positioned in the nitinol and stainless steel tubes, and a second copper wire positioned in the stainless steel tube and the nitinol and stainless steel tubes forming a lap joint therebetween;

FIG. 8 is cross-sectional view of a portion of a fifth embodiment stylet showing the stylet including a distal primary member made of nitinol tube, a proximal secondary member made of stainless steel tube, and a splice overlapping the tubes to form a splice joint therebetween;

FIG. 9 is cross-sectional view of a portion of a sixth embodiment stylet showing the stylet including a distal primary member made of nitinol tube, a proximal secondary member made of stainless steel tube, a first splice overlapping the nitinol tube, and a second splice positioned in the stainless steel tube and the first splice to form a splice joint between the nitinol and stainless steel tubes; and FIG. 10 is cross-sectional view of a portion of a seventh embodiment stylet showing the stylet including a distal primary member made of nitinol tube, a proximal secondary member made of stainless steel tube, a splice overlapped by the nitinol and stainless steel tubes to form a splice joint therebetween, and a copper wire positioned in the nitinol and stainless steel tubes and the splice.

DETAILED DESCRIPTION OF THE DRAWINGS

Figure 1:
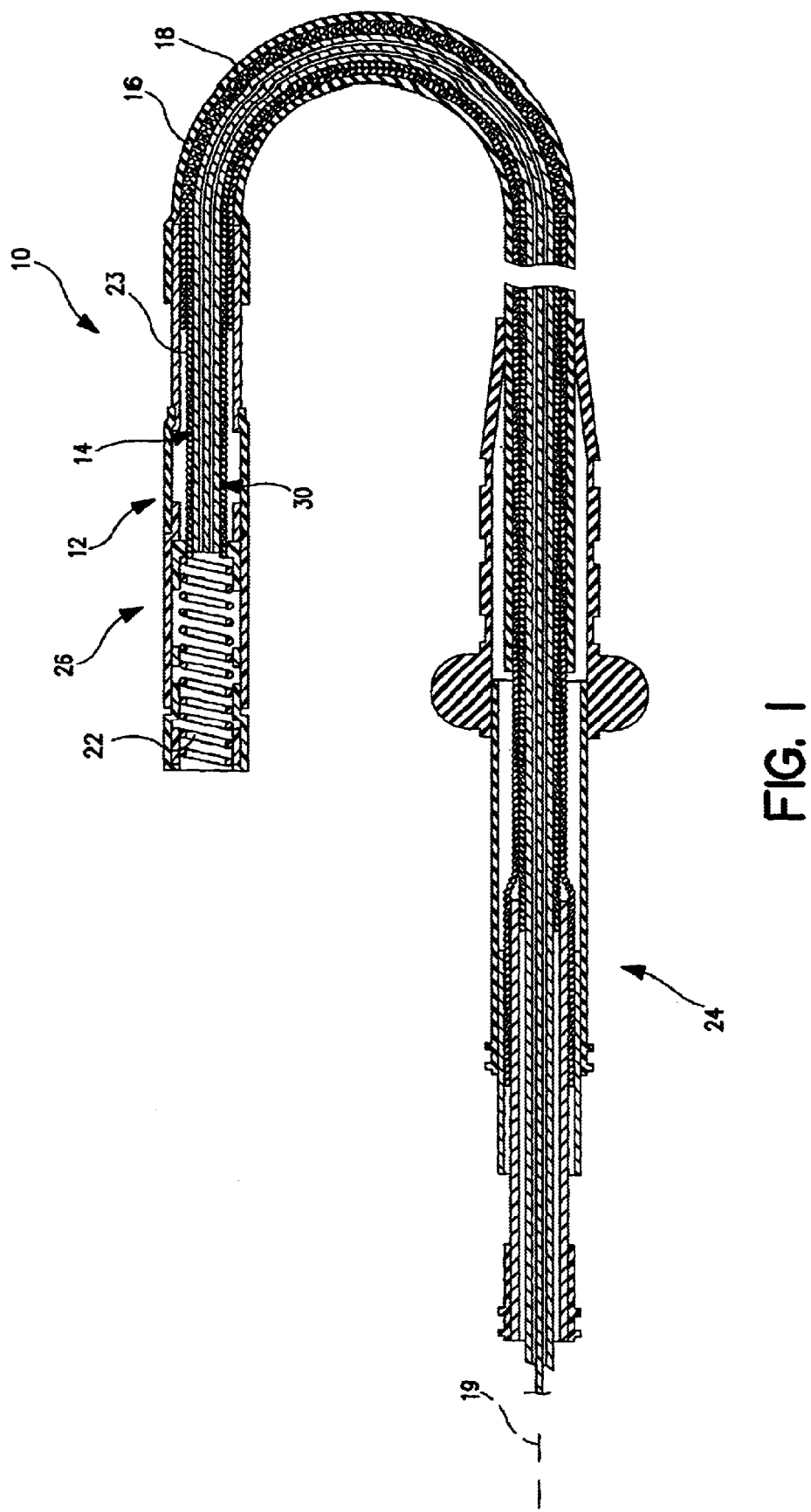
FIG. 1 is a cross-sectional view of a preferred embodiment medical device of present disclosure showing the medical device including a catheter and a stylet positioned in the catheter, and the stylet bending a distal end of the catheter.

As shown in FIG. 1, a preferred embodiment medical device 10 is provided. Medical device 10 includes a catheter 12 and a steerable stylet 14 positioned in catheter 12. Steerable stylet 14 is configured to change the shape of catheter 12 to assist a surgeon in guiding catheter 12 through a passage in a patient.

Figure 2:
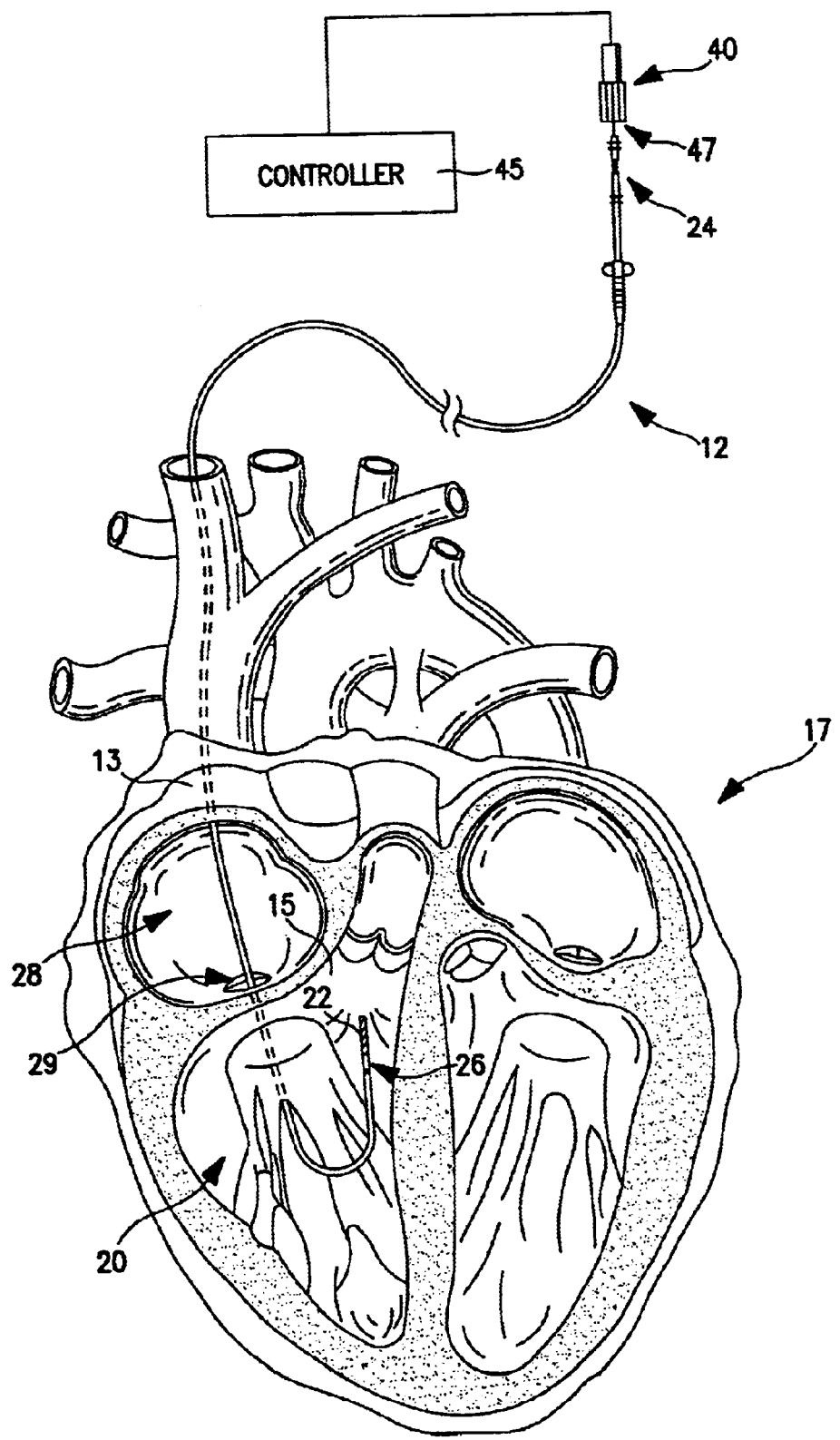
FIG. 2 is a cross-sectional view of a patient's heart showing the medical device inserted into the patient's heart.

According to the preferred embodiment of the present disclosure, catheter 12 is a pacemaker lead. Steerable stylet 14 is configured to assist a cardiologist in guiding pacemaker lead 12 through a patient's heart 17 as shown in FIG. 2. According to alternative embodiments of the present disclosure, the stylet is configured to guide other catheters through other passages in a patient such as a patient's veins, arteries, ducts, or other passages in the patient.

Pacemaker lead 12 is preferable a flexible, elongated tubular member that includes a flexible outer wall 16 that defines a lumen 18 and a central axis 19. Steerable stylet 14 is positioned in lumen 18 to assist in positioning pacemaker lead 12 to a desired location in the right ventricle 20 of heart 17.

According to the preferred embodiment of the present disclosure, pacemaker lead 12 is 60 centimeters long and includes a screw-tip electrode 22 and a lead wire 23 positioned inside flexible outer wall 16. The preferred pacemaker lead 12 is part no. 5076 provided by Medtronic, Inc. of Minneapolis, Minn. Lead wire 23 spirals through lumen 18 of flexible outer wall 16 from a proximal end 24 of pacemaker lead 12 to screw-tip electrode 22 positioned at a distal end 26 of pacemaker lead 12. Lead wire 23 and screw-tip electrode 22 provide an electrical conduit from the pacemaker (not shown) to a muscular chamber wall 15 of right ventricle 20 of heart 17 that is stimulated by the pacemaker. According to alternative embodiments of the present disclosure, bi-polar electrodes having two lead wires, ball-tip pacemaker leads, prong-tip pacemaker leads, open ended catheters such as delivery catheters, closed ended catheters, or any other catheters known to those of ordinary skill in the are used in the medical device.

To position screw-tip electrode 22 in the appropriate location of heart 17, distal end 26 of pacemaker lead 12 must be steered or guided to an entry 13 of heart 17. Distal end 26 is then guided through right atrium 28 and tricuspid valve 29 into right ventricle 20.

Figure 3:
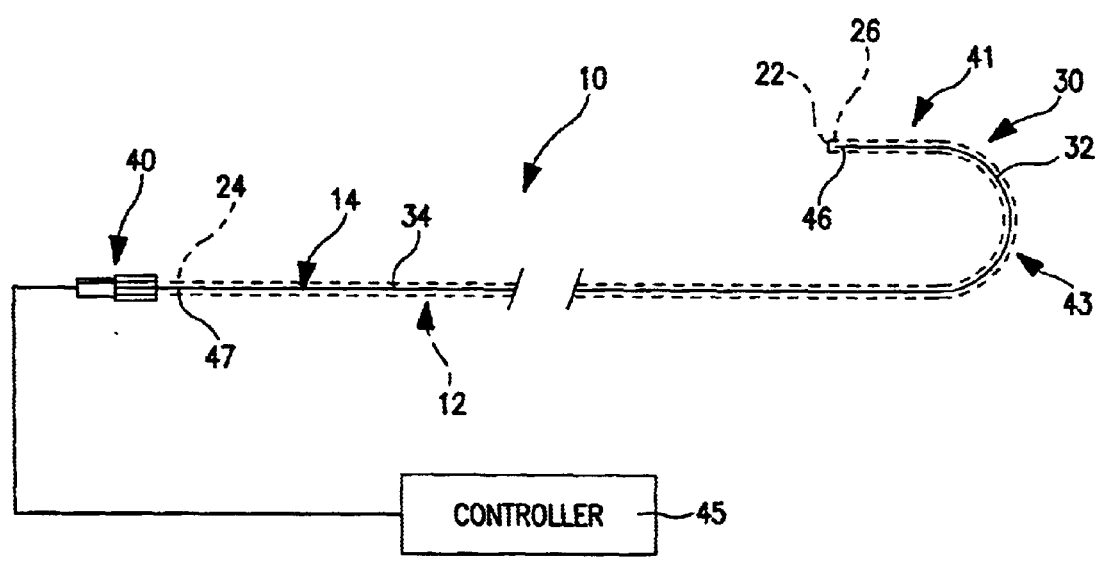
FIG. 3 is a diagrammatic view of the medical device of FIG. 1 showing the stylet bent 180° and the catheter (in phantom) bent 180° by the stylet.

Stylet 14 is specifically configured to steer distal end 26 of pacemaker lead 12 to the preferred attachment location on chamber wall 15 of right ventricle 20 of heart 17 as shown in FIG. 2. To steer distal end 26 to the attachment location, a distal end 30 of stylet 14 is bent to a predetermined shape as shown in FIGS. 1–3. This bending causes distal end 26 of pacemaker lead 12 to also bend so that pacemaker lead 12 "turns" or otherwise positions screw-tip electrode 22 in the appropriate location of heart 17, as shown in FIG. 2. According to alternative embodiments of the present disclosure, stylets are provided that are specifically configured to steer or guide the catheter to other locations in the patient's body.

After screw-tip electrode 22 is positioned adjacent its attachment point within heart 17, screw-tip electrode 22 is pushed into the fibrous tissue of chamber wall 15. The cardiologist then turns lead wire 23 relative to outer wall 16 to thread screw-tip electrode 22 into chamber wall 15. Stylet 14 is then removed from within lumen 18 of pacemaker lead 12 by pulling on proximal end 47 of stylet 14 so that stylet 14 slides relative to pacemaker lead 12. Proximal end 24 of pacemaker lead 12 is then coupled to the pacemaker (not shown).

If during the course of steering pacemaker lead 12 to heart 17, a bend or irregularity is reached where the particular bent shape of primary member 32 is inadequate for steering distal end 26 around said bend, stylet 14 can be removed from pacemaker lead 12 and replaced with another steerable stylet having the appropriate activated shape. For example, if a bend is reached that requires a tighter turn than is possible with stylet 14 shown in FIGS. 1–3, another stylet having a tighter activated shape can be inserted (after the removal of stylet 14) and then activated to negotiate the tighter bend. When stylet 14 is needed, it is positioned back in pacemaker lead 12.

Figure 4:
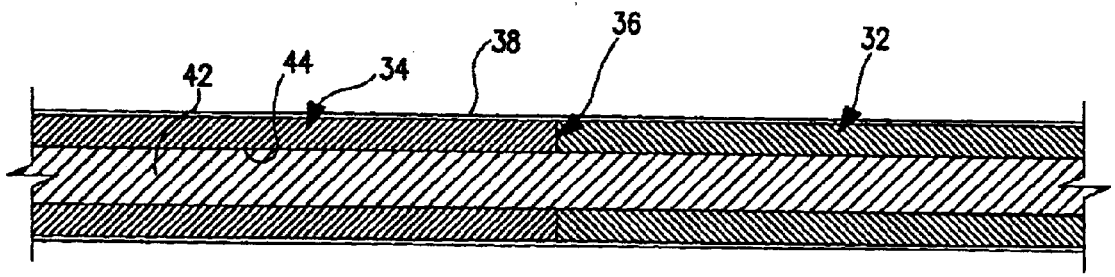
FIGS. 4–10 are cross-sectional views of alternative embodiment stylets showing a junction of primary and secondary tubular members of the stylets.

According to the presently preferred embodiment of the disclosure, distal end 30 of stylet 14 includes a flexible primary member or tube 32 preferably made of a tubular shape-memory material, such as nitinol, and a flexible secondary member or tube 34 preferably made of tubular stainless steel. Stainless steel has a greater modulus of elasticity than nitinol. Primary member 32 terminates short of the proximal end of stylet 14 and pacemaker lead 12. As shown in FIG. 4, primary member 32 is coupled to secondary member 34 to form a butt joint 36 therebetween. Primary member 32 is coupled to secondary member 34 by resistive welding, laser welding, soldering, brazing, swaging, adhesive bonding or any other method of coupling known to those of ordinary skill in the art. Stylet 14 further includes an outer sheath 38 preferably made of an electrically non-conductive material such as polyimide that covers primary and secondary members 32, 34. According to alternative embodiments, other insulative materials such as PET or other materials known to those of ordinary skill in the art are used for the outer sheath.

Shape-memory material is configured to have a first physical characteristic, such as shape or stiffness, under a first condition, such as temperature, and a second physical characteristic, such as a different shape or stiffness, under a second activating condition, such as a higher temperature. For example, primary member 32 has a first shape (straight) when at a first temperature and a second shape (bent as shown in FIGS. 1–3) when activated by heating it to a second higher temperature. Thus, to position screw-tip electrode 22 at the attachment point in heart 17 shown in FIG. 2, primary member 32 is activated to move to the shape shown in FIG. 3 so that pacemaker lead 12 is also bent. Depending on the orientation of primary member 32 relative to the attachment point, medical device 10 or stylet 14 individually may need to be rotated by the cardiologist to ensure that primary member 32 turns toward the attachment location.

According to another example, the primary member made of shape-memory material has a first stiffness at a first temperature and a second greater stiffness when activated by heating it to a second higher temperature. This increase in stiffness permits the physician to push distal end 26 of pacemaker lead 12 through a portion of a passageway that would otherwise resist movement of distal end 26 therethrough. Thus, by heating or otherwise changing a condition of primary member 32, primary member 32 is activated to change one or more of its physical characteristics to aid in steering pacemaker lead 12. According to alterative embodiments of the present disclosure, the primary member is made of other shape-memory materials known to those of ordinary skill in the art.

According to the preferred embodiment of the present disclosure, primary and secondary members 32, 34 have a 0.014 inch (0.356 millimeter) outer diameter and pacemaker lead 12 is 6 French having an 0.078 inch (2 millimeter)

outside diameter. According the preferred embodiment of the present disclosure, primary and secondary members 32, 34 have a 0.007 inch (0.178 millimeter) inside diameter. According to alternative embodiments of the present disclosure, the diameters of the primary member, secondary member, and catheter are smaller or larger. For example, according to one alternative embodiment, the primary member has an outside diameter of 0.050 inches (1.27 millimeters).

As shown in FIG. 3, when in the activated position, primary member 32 includes a straight portion 41 and a semicircular bend portion 43. Straight portion 41 is preferably 2.5 centimeters long and bend portion 43 has a preferred radius of curvature of 1.9 centimeters. According to alternative embodiments of the present disclosure, other deactivated and activated shapes of primary members are provided such as S-curves, spirals, loops, tight turns, loose turns, or other shapes known to those of ordinary skill in the art or necessary to steer, guide, or otherwise position a catheter in a particular location or position.

According to alternative embodiments of the present disclosure, the secondary member is made of copper, silver, nickel, titanium, carbon steel, nitinol, or any other metal or metal alloy known to those of ordinary skill in the art. According to other alternative embodiments of the present disclosure, the secondary member is made of polyimide, polyurethane, PTFE, PVC, or any other non-metallic material known to those of ordinary skill in the art. According to other alternative embodiments of the present disclosure, the secondary member is a solid rod. According to another alternative embodiment of the present disclosure, the primary and secondary members tubes are integral and formed from a single piece of tube.

According to the presently preferred embodiment of the disclosure, primary member 32 is activated by changing the temperature of primary member 32 using an electrical current. An electric potential is created across primary member 32 causing an electric current to pass therethrough. Because of the electrical resistance of primary member 32, the electrical current passing therethrough causes the temperature of primary member 32 to rise and activates primary member 32. This activation causes the shape and/or stiffness of primary member 32 to change. According to alternative embodiments of the present disclosure, the tube is activated by heating the primary member using the body heat of the patient, by aiming radio-frequency or microwave energy at the primary member, by passing warm fluid, such as a saline solution or contrast media, through the primary member, or by any other method of heating or cooling the primary member known to those of ordinary skill in the art.

As shown in FIG. 2, a coupling 40 is provided for electrically coupling stylet 14 to a controller 45. Coupling 40 is coupled to a copper wire or conductor 42 positioned within a lumen 44 defined by primary and secondary members 32, 34. Wire 42 is electrically coupled to a distal end 46 of primary member 32 and electrically isolated from the remainder of primary member 32 and secondary member 34 by a sheath 48 of polyurethane insulation. Secondary member 34 is electrically coupled to coupling 40 and a proximal end 48 of primary member 32 at butt joint 36. According to the preferred embodiment of the present disclosure, wire 42 has a 0.005 inch (0.127 millimeter) outside diameter. According to alternative embodiments, the wire has larger or smaller diameters. According to alternative embodiments, the wire is made of other materials such as stainless steel.

To activate primary member 32 to locate screw-tip electrode 22 at the attachment point, a user operates controller 45 so that an electrical potential is applied to wire 42. According to the preferred embodiment of the present disclosure, controller 45 includes a toggle switch or button movable between a first or on position applying potential to wire 42 and a second of off position with no potential applied to wire 42. According to alternative embodiments of the present disclosure, other configurations of controllers known to those of ordinary skill in the art are provided.

The potential applied to wire 42 causes an electric current to flow through wire 42 to distal end 46 of primary member 32, through primary member 32 to butt joint 36 and secondary member 34, and through secondary member 34 to coupling 40. This electric current causes resistive heating within primary member 32 causing the temperature of primary member 32 to rise. This rise in temperature causes primary member 32 to activate and assume the bent shape shown in FIG. 1 to steer position screw-tip electrode 22 of pacemaker lead 12 the location in heart 17 shown in FIG. 2. To return primary member 32 to its de-activated or unbent shape, enough time is allowed to pass until the energy introduced into primary member 32 by the resistive heating is allowed to dissipate and the temperature of primary member 132 decreases. According to an alternative embodiment of the present disclosure, the shape of the primary member remains substantially constant after activation and the overall stiffness of the primary member increases.

Figure 5:
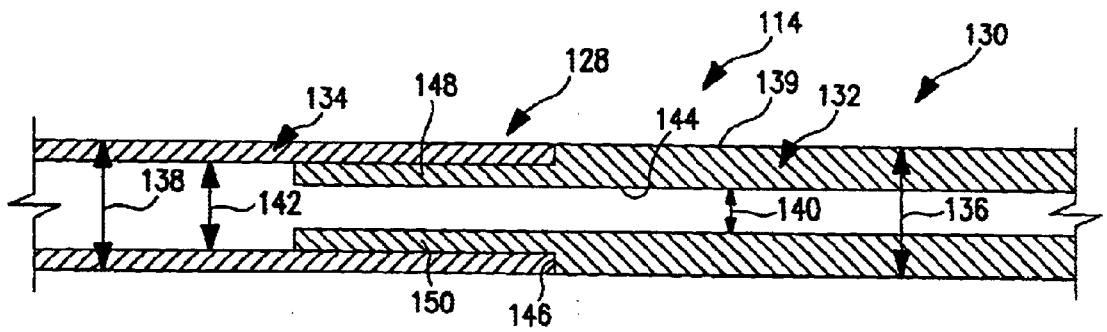

An alternative embodiment stylet 114 is shown in FIG. 5. A distal end 130 of stylet 114 includes a flexible primary member 132 preferably made of a shape-memory material, such as nitinol, and a flexible secondary member 134 preferably made of stainless steel or another material. Primary member 132 is coupled to secondary member 134 to form a lap joint 128 therebetween. Primary and secondary members 132, 134 have outside diameters 136, 138 that are substantially equal. Primary member 132 has in inside diameter 140 that is smaller than an inside diameter 142 of secondary member 134. A proximal end 148 of primary member 132 is ground, machined, or otherwise formed to include an external shoulder 146 and a male portion 150 sized to fit within secondary member 134 so that secondary member 134 overlaps primary member 132. External shoulder 146 and male portion 150 cooperate to define an internal corner in proximal end 148 so that proximal end 148 is stepped. Further, secondary member 134 terminates short of a distal end of primary member 132, Primary member 132 may be coupled to secondary member 134 by resistive welding, laser welding, soldering, brazing, crimping, swaging, friction fitting, press fitting, adhesive bonding, or any other method of coupling known to those of ordinary skill in the art. Stylet 114 further includes an outer sheath 139 that covers primary and secondary members 132, 134. According to an alternative embodiment of the present disclosure, the secondary member is formed to include the external shoulder and male portion so that the male portion thereof is sized to fit in the primary member.

Primary member 132 is activated by passing warm saline or another solution through a lumen 144 defined by primary and secondary members 132, 134. As the warm solution passes through primary member 132, the temperature thereof increases to a level at which activation occurs and primary member 132 tube bends and/or stiffens. To return primary member 132 to its de-activated or unbent shape, a cooler solution is passed through lumen 144 or enough time is allowed to pass until the energy introduced into primary member 132 by the warm solution is allowed to dissipate and the temperature of primary member 132 decreases.

According to an alternative embodiment of the present disclosure, the temperature of primary member 132 is increased by using resistive heating. Outer sheath 138 is provided with a wire electrically coupled to coupling 40 at the proximal end of stylet 114 and to the distal end of primary member 132. Secondary member 134 is also electrically coupled to coupling 40 at the proximal end of stylet 114 and to the proximal end of primary member 132. Thus, an electric potential from the controller is applied across primary member 132 through the wire and secondary member 134 so that an electric current flows therethrough. This flow of electrical current causes the temperature of primary member 132 to rise and primary member 132 to move to the activated position. According to the presently preferred embodiment of the disclosure, the wire is spiral wound around the primary and secondary members. According to another embodiment of the present disclosure, the wire extends axially from the proximal to distal end of the stylet through the outer sheath.

According to another alternative embodiment of the present disclosure, two wires (not shown) are positioned in the outer sheath. A first of the wires is electrically coupled to the distal end of primary member 132 and to coupling 40. A second of the wires is electrically coupled to the proximal end of primary member 132 and to coupling 40. Thus, an electric potential from the controller is applied across primary member 132 through the first and second wires so that an electric current flows therethrough. This flow of electrical current causes the temperature of primary member 132 to rise and primary member 132 to move to the activated position. According to the presently preferred embodiment of the disclosure, the wires are spiral wound around the primary and secondary members. According to another embodiment of the present disclosure, the wires extend axially from the proximal to distal end of the stylet through the outer sheath or are formed in a braid.

According to yet another embodiment of the present disclosure, a metallic coating is applied to the stylet that is electrically insulated from secondary member 134. The metallic coating is electrically coupled to coupling 40 and the distal end of primary member 132. Secondary member 134 is electrically coupled to coupling 40 and the proximal end of primary member 132. Thus, an electric potential from the controller is applied across primary member 132 through the metallic coating and secondary member 134 so that an electric current flows therethrough. This flow of electrical current causes the temperature of primary member 132 to rise and primary member 132 to move to the activated position.

Figure 6:
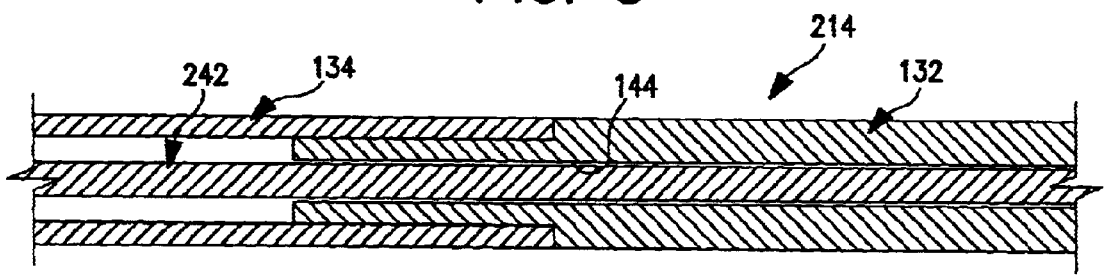

According to another embodiment of the present disclosure, a stylet 214 similar to stylet 114 of FIG. 5 is provided as shown in FIG. 6. Stylet 214 includes a wire 242 positioned within lumen 144. Wire 242 is electrically coupled to coupling 40 at the proximal end of stylet 214 and to the distal end of primary member 132. Secondary member 134 is also electrically coupled to coupling 40 at the proximal end of stylet 214 and to the proximal end of primary member 132. Thus, an electric potential from controller 45 is applied across primary member 132 through wire 242 and secondary member 134 so that an electric current flows therethrough. This flow of electrical current causes the temperature of primary member 132 to rise and primary member 132 to move to the activated position.

Figure 7:
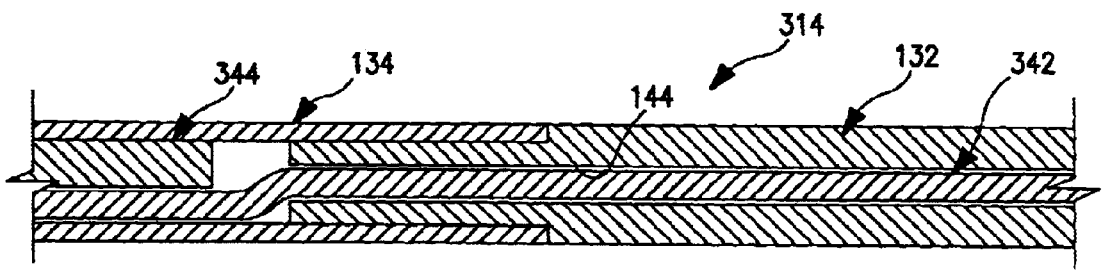

According to another embodiment of the present disclosure, a stylet 314 similar to stylet 114 of FIG. 5 is provided as shown in FIG. 7. Stylet 314 includes first and second wires 342, 344 positioned within lumen 144. First wire 342 is electrically coupled to coupling 40 at the proximal end of stylet 314 and to the distal end of primary member 132. Secondary wire 344 is also electrically coupled to coupling 40 at the proximal end of stylet 214 and to the distal end of secondary member 134. Thus, an electric potential from the controller as supplied through first and second wires 342, 344 is applied across primary member 132 so that an electric current flows therethrough. This flow of electrical current causes the temperature of primary member 132 to rise and primary member 132 to move to the activated position.

Figure 8:
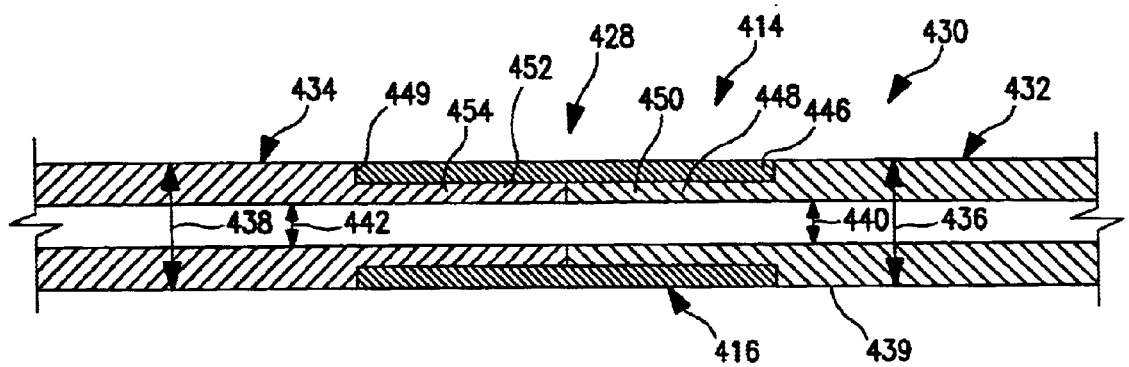

An alternative embodiment stylet 414 is shown in FIG. 8. A distal end 430 of stylet 414 includes a flexible primary member 432 preferably made of a shape-memory material, such as nitinol, and a flexible secondary member 434 preferably made of stainless steel or another material. Stylet 414 further includes a splice or interconnection member 416 overlapping portions of primary and secondary members 432, 434 to form a splice joint 428 coupling primary member 432 to secondary member 434.

Primary and secondary members 432, 434 have outside diameters 436, 438 that are substantially equal and inside diameters 440, 442 that are substantially equal. A proximal end 448 of primary member 432 is ground, machined, or otherwise formed to include an external shoulder 446 and a male portion 450 sized to fit in a distal end of splice 416 so that splice 416 overlaps primary member 432. Similarly, a distal end of secondary member 434 is ground, machined, or otherwise formed to include an external shoulder 449 and a male portion 452 sized to fit in a proximal end of splice 416 so that splice 416 overlaps secondary member 432. Primary and secondary members 432, 434 may be coupled to splice 416 by resistive welding, laser welding, soldering, brazing, crimping, swaging, friction fitting, press fitting, adhesive bonding or any other method of coupling known to those of ordinary skill in the art. Stylet 414 further includes an outer sheath 439 that covers primary and secondary members 432, 434 and splice 416. According to an alternative embodiment of the present disclosure, the primary and secondary members are formed to include internal shoulders so that the splice is sized to fit within the primary and secondary members. Primary member 432 is activated using any of the techniques described herein such as using a warm solution, radio-frequency or microwaves, electrical resistance heating, or any other activating technique known to those of ordinary skill in the art.

Figure 9:
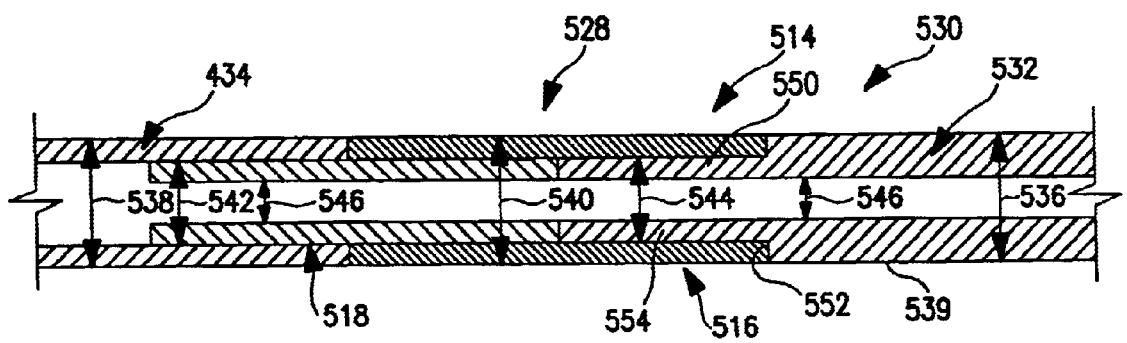

An alternative embodiment stylet 514 is shown in FIG. 9. A distal end 530 of stylet 514 includes a flexible primary member 532 preferably made of a shape-memory material, such as nitinol. Stylet 514 further includes a flexible secondary member 434 preferably made of stainless steel or another material and first and second splices 516, 518. First splice 516 overlaps a proximal end of primary member 532 and a distal end of second splice 518. Secondary member 534 overlaps a portion second splice 518. Thus, primary member 532 is coupled to secondary member 534 by a double splice joint 528.

Primary and secondary members 532, 534 and first splice 516 have outside diameters 536, 538, 540 that are substantially equal. Secondary member 534 and first splice 516 have inside diameters 542, 544 that are substantially equal and primary member 532 and second splice 518 have inside diameters 546, 548 that are substantially equal. A proximal end 550 of primary member 532 is ground, machined, or otherwise formed to include an external shoulder 552 and a male portion 554 sized to fit within a distal end of first splice 516 so that first splice 516 overlaps primary member 532 and second splice 518 and secondary member 534 also overlaps second splice 518. Primary member 532 and first splice 516, first splice 516 and second splice 518, and secondary member 534 and second splice 518 may be coupled by resistive welding, laser welding, soldering, brazing, crimping, swaging, friction fitting, press fitting, adhesive bonding or any other method of coupling known to those of ordinary skill in the art. Stylet 514 further includes an outer sheath 539 that covers primary and secondary members 532, 534 and first and second splices 516, 518. According to alternative embodiments of the present disclosure, the radial orientation of the first and second splices are different from those illustrated in FIG. 9. For example, according to another alterative embodiment, the secondary member (with or without an internal shoulder and female portion) is positioned radially inward of the second splice and the first splice is positioned radially inward of the second splice and the primary member secondary member (with or without an external shoulder and male portion).

Primary member 532 is activated using any of the techniques described herein such as using a warm solution, radio-frequency or microwaves, electrical resistance heating, or any other activating technique known to those of ordinary skill in the art. For example, according to one embodiment, a wire internal or external of the lumen defined by secondary and primary members 532, 534 is electrically coupled to coupling 40 and the distal end of primary member 532. The proximal end of secondary member 534 is electrically coupled to coupling 40 and to the proximal end of primary member 532 through first and second splices 516, 518 to supply an electric potential across primary member 532. According to other embodiments, the second wire maybe coupled to either splice or directly to the proximal end of primary member 532.

Figure 10:
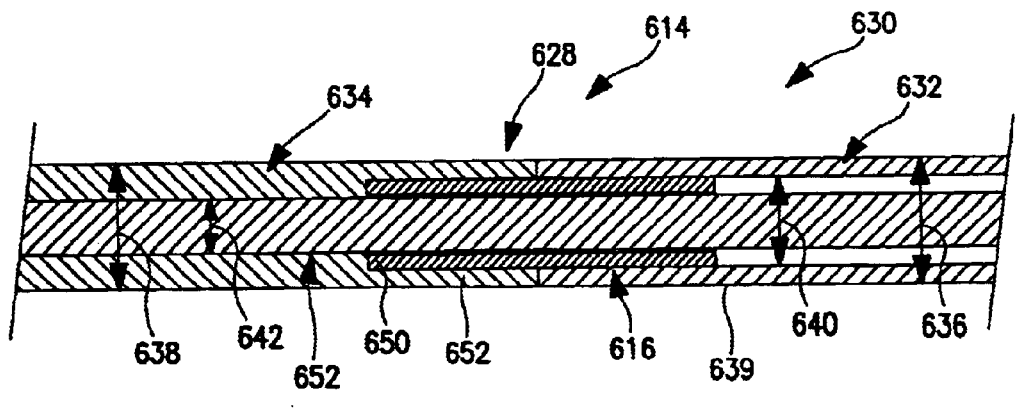

Another alternative embodiment stylet 614 is shown in FIG. 10. A distal end 630 of stylet 614 includes a flexible primary member 632 preferably made of a shape-memory material, such as nitinol, and a flexible secondary member 634 preferably made of stainless steel or another material. Stylet 614 further includes a splice 616 overlapped by portions of primary and secondary members 632, 634 to form a splice joint 628 coupling primary member 632 to secondary member 634.

Primary and secondary members 632, 634 have outside diameters 636, 638 that are substantially equal. Inside diameter 640 of primary member 632 is greater than inside diameter 642 of secondary member 634. Inside diameter 640 is sized so that a proximal end of primary member 632 fits over a distal end of splice 616 so that primary member 632 overlaps splice 616. A distal end of secondary member 634 is ground, machined, or otherwise formed to include an internal shoulder 650 and a female portion 652 sized to fit over a proximal end of splice 616 so that secondary member 634 overlaps splice 616. Primary and secondary members 632, 634 may be coupled to splice 616 by resistive welding, laser welding, soldering, brazing, crimping, swaging, friction fitting, press fitting, adhesive bonding or any other method of coupling known to those of ordinary skill in the art. Stylet 614 further includes an outer sheath 639 that covers primary and secondary members 632, 634. According to an alternative embodiment of the present disclosure, at least one of the secondary and primary members are formed to include an external shoulder so that the splice is sized to overlap at least one of the primary and secondary members.

Primary member 632 is activated using any of the techniques described herein such as using a warm solution, radio-frequency or microwaves, electrical resistance heating, or any other activating technique known to those of ordinary skill in the art. For example, stylet 616 includes a wire 652 electrically coupled to coupling 40 and a distal end of primary member 632. Secondary member 634 is electrically coupled to coupling 40 and a proximal end of primary member 632 so that an electric current passes through and heats primary member 632. Preferably, if a warm solution is used to activate primary member 632, wire 652 is not provided so that the warm solution can more freely travel through the lumen defined by primary and secondary members 632, 634.

Although the invention has been described in detail with reference to preferred embodiments, variations and modifications exist within the scope and spirit of the invention as described and defined in the following claims.

What is claimed is:

1. A device comprising
   a flexible, elongated tubular member having a central axis extending therethrough and
   a stylet having a shape-memory tube made of shape-memory material and formed to include a lumen extending therethrough, the shape-memory tube being positioned in the tubular member to permit movement of the shape-memory tube relative to the tubular member along the central axis, the movement of the shape-memory tube relative to the tubular member along the central axis occurring during insertion or removal of the stylet into or out of the tubular member during a medical procedure.

2. The device of claim 1, wherein the shape-memory tube is configured to move between an activated position and a deactivated position.

3. The device of claim 1, wherein the tubular member includes a distal end and a proximal end and the shape-memory tube terminates short of the proximal end of the tubular member.

4. The device of claim 1, wherein the stylet further includes an electrical conductor positioned in the lumen of the shape-memory tube.

5. The device of claim 1, wherein the stylet further includes a secondary tube coupled to the shape-memory tube, the secondary tube is positioned in the tubular member, and the secondary tube is made of a different material than the shape-memory tube.

6. The device of claim 5, wherein the secondary tube is electrically coupled to the shape-memory tube.

7. The device of claim 5, wherein the secondary tube and the shape-memory tube am coupled together by a splice joint.

8. The device of claim 7, wherein the secondary tube and shape-memory tube overlap.

9. The device of claim 7, wherein the stylet further includes an interconnection member and one of the interconnection member and the secondary and shape-memory tubes overlap.

10. The device of claim 1, wherein the shape-memory tube moves between a first position when at a first temperature and a second position different than the first position when at a second temperature different than the first temperature and the movement of the shape-memory tube causes a distal end of the tubular member to deflect.

11. The device of claim 1, wherein the shape-memory tube has a first stiffness when at a first temperature and a second stiffness that is greater than the first stiffness when a second temperature.

12. The device of claim 1, wherein a proximal end of the shape-memory tube is configured to couple to an electrical coupling.

13. A device comprising
a tubular member having a lumen formed therein and
a shape-memory member having a lumen formed therein, the shape-memory member being received in the lumen of the tubular member and configured for removal from the lumen, the shape-memory member being movable in response to a change in temperature of the shape-memory member, the shape of the tubular member changing upon movement of the shape-memory member.

14. The device of claim 13, wherein the shape-memory member is configured to slide relative to the tubular member during insertion and removal of the shape-memory member from the tubular member.

15. The device of claim 13, wherein the shape-memory member is positioned in a distal end of the tubular member.

16. The device of claim 13, wherein the tubular member has a proximal end and a distal end and the distal end is closed.

17. The device of claim 13, further comprising first and second conductors, wherein the first conductor is coupled to a proximal end of the shape-memory member and the second conductor is coupled to a distal end of the shape-memory member.

18. The device of claim 17, wherein the second conductor is positioned within the shape-memory member.

19. The device of claim 13, further comprising a secondary tube removably received in the lumen of the tubular member and made a different material than the shape-memory member.

20. The device of claim 19, wherein the secondary tube abuts the shape-memory member.

21. The device of claim 19, wherein the secondary tube is electrically coupled to the shape-memory member.

22. The device of claim 19, wherein the secondary tube is coaxial with the shape-memory tube.

23. The device of claim 19, wherein the secondary tube is spliced with the shape-memory member.

24. The device of claim 19, wherein the tubular member is an electrical lead.

25. A device configured to be inserted into a passage, the device comprising
a catheter formed to include a lumen therein and
a stylet insertable into the lumen of the catheter and having a tubular member made of a shape-memory material configured to alter a physical characteristic of the catheter in response to activation of the shape-memory material.

26. The device of claim 25, wherein the catheter is elongated.

27. The device of claim 26, wherein the catheter is flexible.

28. The device of claim 25, wherein the stylet deflects the catheter upon activation of the shape-memory material.

29. The device of claim 25, wherein the stylet changes the stiffness of the catheter upon activation of the shape-memory material.

30. The device of claim 25, wherein the stylet has a first end and a second end spaced apart from the first end and the tubular member terminates short of the first end.

31. The device of claim 30, wherein the stylet further includes a secondary member extending between the tubular member and the first end.

32. The device of claim 31, wherein the stylet further includes means for coupling the secondary member to the tubular member.

33. The device of claim 25, wherein the shape-memory material is temperature activated.

34. The device of claim 31, wherein the shape-memory material changes shape upon activation.

35. The device of claim 31, wherein the shape-memory material changes stiffness upon activation.

36. The device of claim 25, wherein the catheter is electrically conductive.

37. A medical device configured to be inserted into a passage of a patient, the medical device comprising
a flexible, elongated member having a distal end configured to be inserted into a passage of a patient and a proximal end spaced apart from the distal end, the flexible, elongated member including a primary member, a secondary member, and means for coupling the primary member to the secondary member, the primary member having a lumen formed therein and being made of a shape-memory material, the primary member being made of a first material having a first modulus of elasticity, the secondary member being made of a second material having a second modulus of elasticity that is greater than the first modulus of elasticity.

38. The device of claim 37, wherein the secondary member extends between the primary member and the proximal end.

39. The device of claim 37, wherein the flexible, elongated member further includes a central axis that extends through the primary and secondary members.

40. The device of claim 37, wherein the coupling means electrically couples the primary member to the secondary member.

41. The device of claim 37, wherein the coupling means comprises a butt joint.

42. The device of claim 37, wherein the coupling means comprises a splice joint.

43. The device of claim 37, wherein the coupling means comprises a lap joint.

44. The device of claim 37, further comprising a flexible, elongated catheter having a lumen formed therein, the flexible, elongated member being received within the catheter for ready removal, and the primary member being configured to change a physical characteristic of the catheter upon activation of the shape memory material of the primary member.

45. A medical device configured to be inserted into a passage of a patient, the medical device comprising
a flexible elongated catheter having a lumen formed therein, and
a flexible, elongated member having a distal end configured to be inserted into a passage of a patient and a proximal end spaced apart from the distal end, the flexible, elongated member including a primary member and a secondary member coupled to the primary member, the primary member having a lumen formed therein and being made of a shape-memory material, the secondary member being made of an electrically conductive material, the flexible, elongated member being received within the catheter for contemporaneous removal from the catheter and passage of the patient, and the primary member being configured to change a physical characteristic of the catheter upon activation of the shape-memory material of the primary member.

46. The device of claim 45, wherein the secondary member extends between the primary member and the proximal end.

47. The device of claim 45, wherein the flexible, elongated member further includes a central axis that extends through the primary and secondary members.

48. The device of claim 45, wherein the secondary member is electrically coupled to the primary member.

49. The device of claim 45, wherein the primary and secondary members cooperate to define a butt joint therebetween.

50. The device of claim 45, wherein the flexible elongated member further includes a splice configured to couple the primary member to the secondary member.

51. The device of claim 45, wherein the primary and secondary members cooperate to define a lap joint therebetween.

52. The device of claim 45, wherein the secondary member includes a lumen.

53. The device of claim 52, wherein the lumen of the secondary member aligns with the lumen of the primary member.

54. The device of claim 45, wherein the secondary member is solid.

55. A medical device configured to be inserted into a passage of a patient, the medical device comprising a flexible, elongated member having a distal end configured to be inserted into a passage of a patient and a proximal end spaced apart from the distal end, the flexible, elongated member including a primary member and a secondary member coupled to the primary member, the primary member having a lumen formed therein and being made of a shape-memory material, the secondary member being made of a metallic material, the primary member including a proximal end and a distal end, the secondary member terminating short of the distal end of the primary member.

56. The medical device of claim 55, wherein the proximal end is stepped.

57. The medical device of claim 55, wherein the primary member and the secondary member are coupled together by a weld.

\* \* \* \* \*